United States Patent [19]

Bentz

[11] 4,240,286
[45] Dec. 23, 1980

[54] VISCOSIMETER

[75] Inventor: Allan J. Bentz, Guilford, N.Y.

[73] Assignee: Simmonds Precision Products, Inc., Tarrytown, N.Y.

[21] Appl. No.: 50,580

[22] Filed: Jun. 21, 1979

[51] Int. Cl.³ .......................................... G01N 11/14
[52] U.S. Cl. ......................................................... 73/59
[58] Field of Search ................................ 73/54, 59, 60

[56] References Cited

U.S. PATENT DOCUMENTS

| 2,410,385 | 10/1946 | Loukomsky et al. | 73/59 |
| 3,886,789 | 6/1975 | Brookfield | 73/59 |
| 4,148,216 | 4/1979 | Do et al. | 73/59 |

FOREIGN PATENT DOCUMENTS 389441  11/1973  U.S.S.R. ........................................ 73/59

Primary Examiner—Gerald Goldberg
Assistant Examiner—Joseph W. Roskos
Attorney, Agent, or Firm—Edwin E. Greigg

[57] ABSTRACT

A viscosimeter for measuring the viscosity of liquids and, in particular, viscous material such as polyester resins and the like which includes a rotatably driven cup in which the liquid sample to be measured is introduced and heated and a torsion wire and spindle assembly suspended from an upstanding support with a plunger mounted on the lower end of the assembly by means of a thermal isolation coupler for immersion in the sample, the support being provided with an adjustment mechanism including a clamp for positioning the plunger in a calibrated position within the sample together with a capacitive-type transducer connected to an electronic readout circuit whereby rotation of the cup rotates the torsion wire and spindle assembly due to the drag of the liquid until the restoring force of the torsion wire just balances the drag of the liquid to provide a readout from the readout circuit corresponding to the viscosity of the liquid.

5 Claims, 9 Drawing Figures

VISCOSIMETER

BACKGROUND OF THE INVENTION

A well known type of viscosimeter utilizes a cup mounted on a rotating hot plate into which the liquid sample to be tested is introduced and in which a plunger is immersed, the plunger being mounted on the lower end of a torsion wire and spindle assembly suspended at its upper end from a pylon. The spindle is provided with a dial so that as the cup containing the liquid sample is rotated, the spindle and torsion wire assembly rotates also due to the drag of the liquid on the plunger. The spindle rotates until the restoring force of the torsion wire just balances the drag of the liquid and when the dial stops the reading taken therefrom can be converted into centipoises. One such type of viscosimeter is manufactured by the Fisher Scientific Company of Pittsburgh, Pennsylvania.

Such present day apparatus for measuring viscosity is characterized by a number of disadvantages. One fundamental flaw in such a viscosimeter is that the large mass of metal used in the shaft by means of which the plunger is attached to the torsion and spindle assembly removes heat from the rotating cup at such a rate that the resulting thermal gradients set up in the cup make the apparent viscosity readings erratic. The elevated temperature in the cup also causes a rapid transmission of heat to the torsion wire changing the torsional restoring force in the wire and invalidating the low temperature calibration required for accurate viscosity readings. Furthermore, where relatively viscous materials such as polyester resins are tested for viscosity in such an apparatus, the thermal expansion of the resin presented a problem in maintaining a constant immersion level of the plunger in the resin. For instance, as the plunger shaft is provided with a calibration mark which must be observed when making viscosity measurements and when using the small sample adaptor in such an apparatus, maintaining the exact immersion is critical. This is because the diameter of the plunger as it emerges from the liquid is the same as the diameter of the plunger below the liquid level. As a result, it is very difficult to make measurements reproducible to plus or minus 5% even if the calibration mark is clearly visible.

Another problem in the use of the aforementioned prior art apparatus is its limitation as to utility in making room temperature viscosity measurements. It is necessary that the entire spindle and plunger assembly be removed in order to change samples and when fine torsion wire is used, a high incidence of breakage and damage to the torsion wire is present even if extreme care is taken in such a procedure.

Another problem area in such prior art apparatus is in the readout mechanism which utilizes a dial and indicator arrangement. Such a dial arrangement presents a problem in setting the rest point to zero, a very difficult and time consuming procedure especially when fine torsion wire is used. Furthermore, reading the scale on the dial is difficult as a result of poor resolution of the printing on the scale, parallax and the harmonic oscillations of the spindle. Although such prior art apparatus utilizes an oil damper for damping such oscillations, it is cumbersome to use and not very effective. Furthermore, the damper contributes substantially to torsion wire damage.

OBJECTS AND SUMMARY OF THE INVENTION

Accordingly, a primary object of this invention is to provide a new and novel viscosimeter which provides highly accurate viscosity measurements on a wide variety of liquids particularly highly viscous liquids such as polyester resins and the like.

Another object of this invention is to provide a new and novel viscosimeter of the type which utilizes a torsion wire suspended plunger immersed in a liquid sample contained in a rotatable heated cup which permits the use of elevated temperatures in the cup with virtually no effect on the torsion wire or on the viscosity measurements obtained thereby.

A further object of this invention is to provide a new and novel viscosimeter utilizing a torsion wire suspended plunger immersed in a liquid sample contained in a rotating heated cup which produces highly accurate viscosity measurements throughout a wide range of sample temperatures and in which the depth of the plunger in the sample may be easily adjusted.

A still further object of this invention is to provide a new and novel viscosimeter of the torsion wire type utilizing a plunger immersed in a liquid sample contained within a rotating heated cup wherein samples to be tested may be easily changed without exposing the torsion wire and other parts of the apparatus to breakage or damage.

A still further object of this invention is to provide a new and novel viscosimeter which utilizes an electronic readout circuit which permits the unit to be easily zeroed, which incorporates electronic damping to eliminate troublesome oscillations from the output signal and which provides a clear and highly accurate readout of viscosity of the liquid sample measured.

The objects of this invention and other related objects are accomplished by the provision of a base on which a container for the liquid to be tested is rotatably mounted with means for heating the liquid in the container. An upstanding support member having an upper end is provided on the base on which a torsion wire is detachably mounted at its upper end in a vertically extending position and with a vertically extending spindle operatively attached thereto together with a plunger mounted on the lower end of the torsion wire by means of a thermal isolation coupler for immersion in the liquid in the container. The support member includes an adjustment mechanism by means of which the level of the plunger in the liquid may be readily adjusted and the capacitive-type transducer is operatively associated with the spindle for electrically sensing the angular position of the spindle and torsion wire to provide an output signal with electronic readout means connected to the transducer for indicating the viscosity of the liquid in the container.

Other objects and advantages of the present invention will be more readily apparent from a further consideration of the following detailed description of the drawings illustrating a preferred embodiment of the invention, in which:

DESCRIPTION OF THE PREFERRED EMBODIMENT

Figure 1:
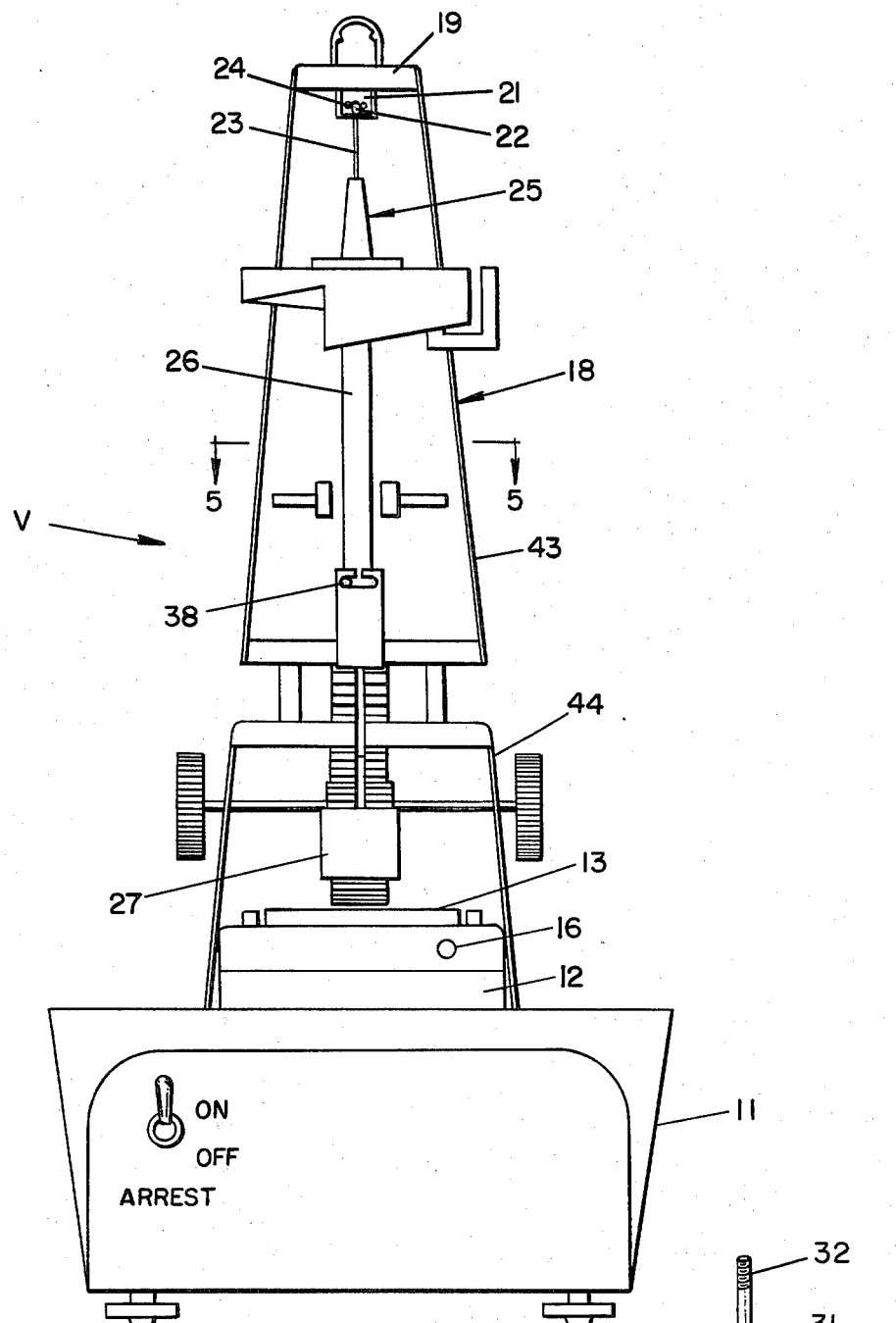
FIG. 1 is a front elevation view of the viscosimeter of the invention.

Referring now to the drawings and to FIG. 1 in particular, there is shown a viscosimeter constructed in accordance with the invention and designated generally by the letter V. The viscosimeter V is contructed in some respects similar to the aforementioned viscosimeter marketed by Fisher Scientific Company but incorporates the many novel features of the invention.

In general, the viscosimeter V includes a base 11 on the upper surface of which is arranged a rotating hot plate 12 arranged to be driven by a motor (not shown) within the base 11. The rotating hot plate 12 is arranged to support a container or cup 13 in which the liquid sample, whose viscosity is to be measured, is introduced. The rotating hot plate 12 is provided with a suitable heater and heater control such as a thermostat 16 for heating the liquid sample in the cup 13 to the selected temperature and the temperature of the sample may be adjusted by means of the thermostat 16.

The viscosimeter V also includes an upstanding support member or pylon 18 suitably supported at its lower end on the base 11. The upper end of the pylon 18 is provided with a horizontally extending portion 19 on which is supported a bracket 21 having a slot 22 for detachably accommodating the upper end of a relatively thin torsion wire 23 so that the torsion wire 23 is disposed in a vertically extending position. Preferably, the torsion wire 23 includes a head 24 for retaining the upper end of the torsion wire in the slot 22.

The lower end of the torsion wire 23 is adapted to support a plunger 27 which is immersed in the liquid in the cup 13 at a selected level in a well known manner. The viscosimeter V also includes a spindle 26 which is attached in a vertically extending manner as shown in FIG. 1 to the torsion wire 23, the spindle 26 being hollow to provide an inner bore through which the torsion wire 23 extends.

Figure 2:
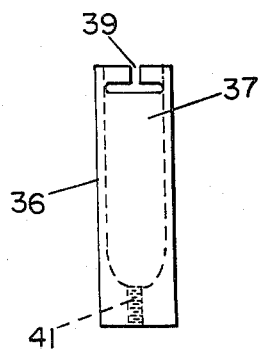
FIG. 2 is an elevation view of the thermal isolation coupler utilized in the viscosimeter of FIG. 1.
Figure 3:
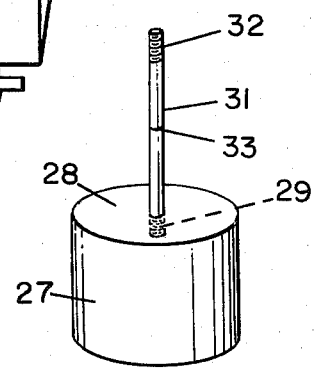
FIG. 3 is an elevation view of the plunger and shaft incorporated in the viscosimeter of FIG. 1.

Referring now to FIGS. 2 and 3, there is shown in FIG. 3 the plunger 27 which is preferably of cylindrical shape and formed of highly polished stainless steel, the dimensions of the plunger being selected in accordance with the viscosity range to be measured and the gauge of the torsion wire 23. The plunger 27 includes an upper end face 28 provided with an internally threaded axial recess 29 for accommodating the externally threaded end of a connecting rod 31. The connecting rod 31 includes an externally threaded upper end portion 32 and a suitably inscribed calibration mark 33 which is used in conjunction with the level of liquid within the cup 13 to position the plunger 27 at the proper level in the cup 13.

In order to couple the plunger 27 to the spindle 26, a thermal isolation coupler 36 is utilized, as shown best in FIG. 2, which is of heat insulation material such as fiberglass, teflon, or the like. The coupler 36 is provided with an inner bore 37 to accommodate the lower end of the spindle 26 provided with a lug 38, as shown in FIG. 1. The lower end of the spindle 26 is accommodated within the bore 37 and the lug 38 on the spindle is inserted in a slot 39 provided in the upper end of the coupler 36. At the other end of the coupler 36, the bore 37 is of reduced diameter to provide an internally tapped recess 41 for threaded engagement with the threaded portion 32 on the plunger shaft 31.

The relatively small diameter of the plunger shaft 31 and the provision of the coupler 36 of heat insulation material thereby greatly reduces or substantially eliminates the transfer of heat from the plunger 27 (immersed in the heated liquid) to the torsion wire and spindle assembly 25 so that the heat loss problem characteristic of prior art viscosimeters is greatly reduced. Furthermore, the use of the shaft 31 and coupler 36 and attendant blocking of the transfer of heat eliminates any effect of heat on the torsion wire 23 and the removal of heat from the liquid in the cup 13 thereby permitting accurate low temperature calibration. The small diameter of the plunger shaft 31 makes only a small contribution to the total torque. It is only important that the distance from the bottom of the plunger to the bottom of the cup 13 and the distance from the top 28 of the plunger 27 to the surface of the liquid in the cup 13 be significantly greater than the distance from the vertical surface of the plunger to the vertical surface of the cup 13.

The viscosimeter V also includes adjustable means for adjusting the level of the plunger 27 in the cup 13 and for easy changing of liquid samples in the cup. As shown best in FIGS. 1 and 4, the support member or pylon 18 includes an upper section 43 and a lower section 44, the upper section 43 being arranged for adjustable vertical movement relative to the lower section 44. More specifically, the upper pylon section 43 includes a plate 46 having a pair of openings 47, 48 which accommodate guide posts 51, 52, respectively. The guide posts 51, 52 are mounted in a vertically extending spaced-apart relationship at their lower ends on a plate 53 suitably mounted in the lower pylon section 44, as shown best in FIG. 4.

A plate 53 is provided with a notch 54 which accommodates a vertically extending rack 56, the upper end of which engages the underside of the plate 46 on the upper pylon section 43. The rack 56 is arranged to be moved reciprocally in a vertical direction by means of a pinion 57, the teeth of which engage the teeth of the rack 56 in the well known manner. The pinion 57 is mounted on a horizontally extending shaft 58 at the opposite ends of which are provided knurled knobs 61, 62.

Figure 4:
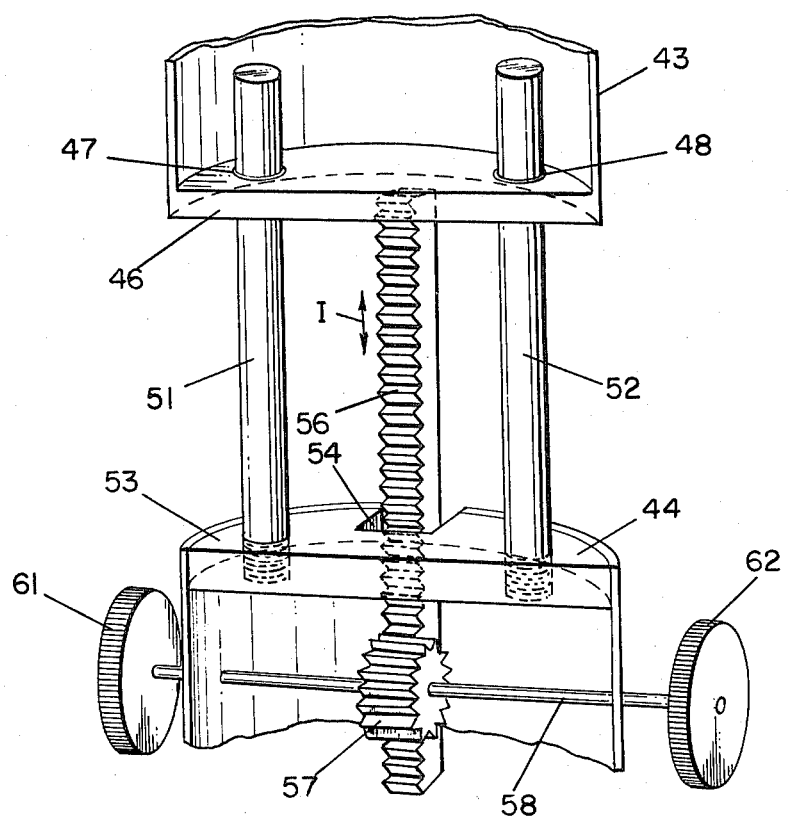
FIG. 4 is an enlarged perspective view of the plunger height adjustment mechanism incorporated into the viscosimeter of FIG. 1.

As shown in FIG. 1, the knurled knobs 61, 62 extend laterally outward on opposite sides of the pylon 18 and may be manually rotated to rotate the pinion 57 and move the rack 56 in the direction of the double arrow I of FIG. 4.

Figure 5:
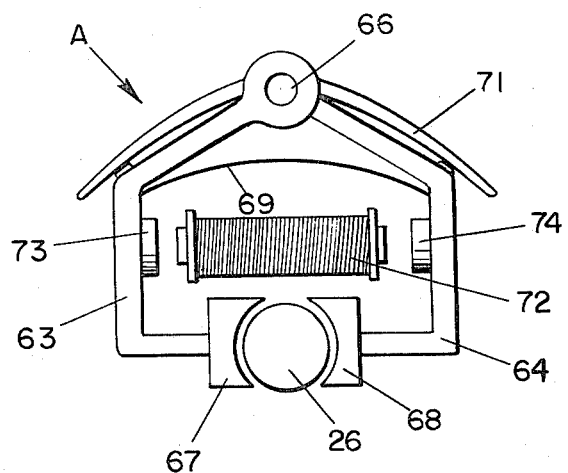
FIG. 5 is a sectional view taken substantially along line 5—5 of FIG. 1 in the direction of the arrows.
Figure 6:
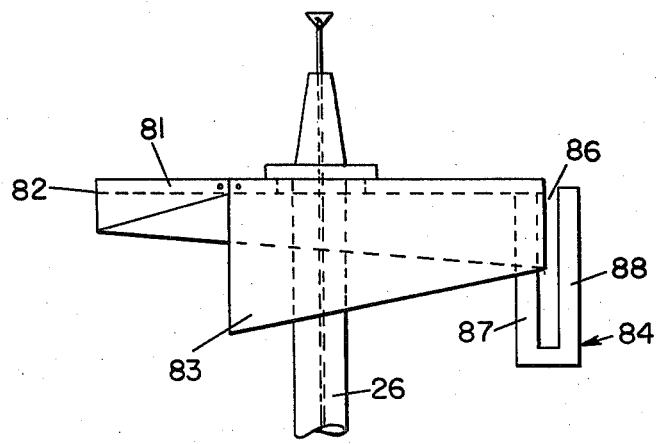
FIG. 6 is an enlarged view of an upper portion of the viscosimeter of FIG. 1 illustrating the capacitive-type transducer incorporated in the invention.

In conjunction with the immersion adjusting mechanism of FIG. 4, the viscosimeter V includes an arrest mechanism designated generally by the letter A in FIG. 5. As shown in FIG. 5, the arrest mechanism A is in the form of caliper brakes which include a pair of clamping arms 63, 64 pivotally mounted on a common shaft 66 on the pylon upper section 43, as shown in FIG. 1. The free ends of the clamping arms 63, 64 are provided with brake shoes 67, 68 movable together into engagement with the spindle 26, the clamping arms 63, 64 being spring loaded outwardly out of engagement with the spindle 26 by means of a leaf spring 69. The clamping arms 63, 64 are yieldingly urged outwardly in opposite directions by means of the spring 69 against stop means such as an arcuate member 71, as shown in FIG. 5.

In order to actuate the arrest mechanism A, a solenoid 72 is provided between the clamping arms 63, 64 which is suitably connected to an associated source of power. Iron plates 73, 74, serving as armatures, are mounted on the inner side of the clamping arms 63, 64, respectively, which armatures 73, 74 are disposed adjacent the respective end of the solenoid 72. Therefore, when the solenoid is energized, the armatures 73, 74 are attracted thereto moving the clamping arms 63, 64 together with the brake shoes 67, 68 in clamping engagement with the spindle shaft 26.

Thus, with the arrest mechanism A of FIG. 5 the torsion wire and spindle assembly 25 may be locked in an adjusted vertical position during adjustment of the height of the upper pylon section 43 so that the cup 13 and liquid samples therein may be changed easily without damage to the torsion wire 23. Furthermore, the immersion adjusting mechanism of FIG. 4 permits the level of the plunger 27 in the sample liquid in the cup 13 to be adjusted for height utilizing the calibration mark 33 on the plunger shaft 31.

Referring now to FIGS. 6-9, the viscosimeter V includes a transducer and an electronic readout means by means of which the measured viscosity of the liquid sample in a cup 13 may be obtained. More specifically, the spindle 26 is provided at its upper end with a plate or drum 81 suitably secured thereto having a peripheral edge 82 around which is wrapped a linear ramp 83 of metallic material such as sheet metal or the like. Transducer means are associated with the ramp 83 which includes a capacitor 84 of U-shaped configuration having a central gap 86 for accommodating the ramp 83 as shown best in FIGS. 6, 7 and 9. The capcitor 84 includes a pair of active electrodes 87, 88 spaced apart to provide the gap 86 with an insulator 89 therebetween.

Preferably, opposite sides of the capacitor plates 87, 88 are provided with U-shaped guard electrodes 91, 92 separated from the active plates or electrodes 87, 88 by insulators 93, 94. As shown best in FIG. 9, rotation of the spindle 26 into an angular position representative of the viscosity of the measured liquid masks more or less of the electrodes 87, 88 and, as the ramp 83 is held at ground potential, its presence between the electrodes 87, 88 reduces the capacitance of the transducer in direct proportion to the area which is masked. The guard electrodes 91, 92 serve only to contain fringe fields, thereby reducing proximity effects and improving linearity.

Figure 8:
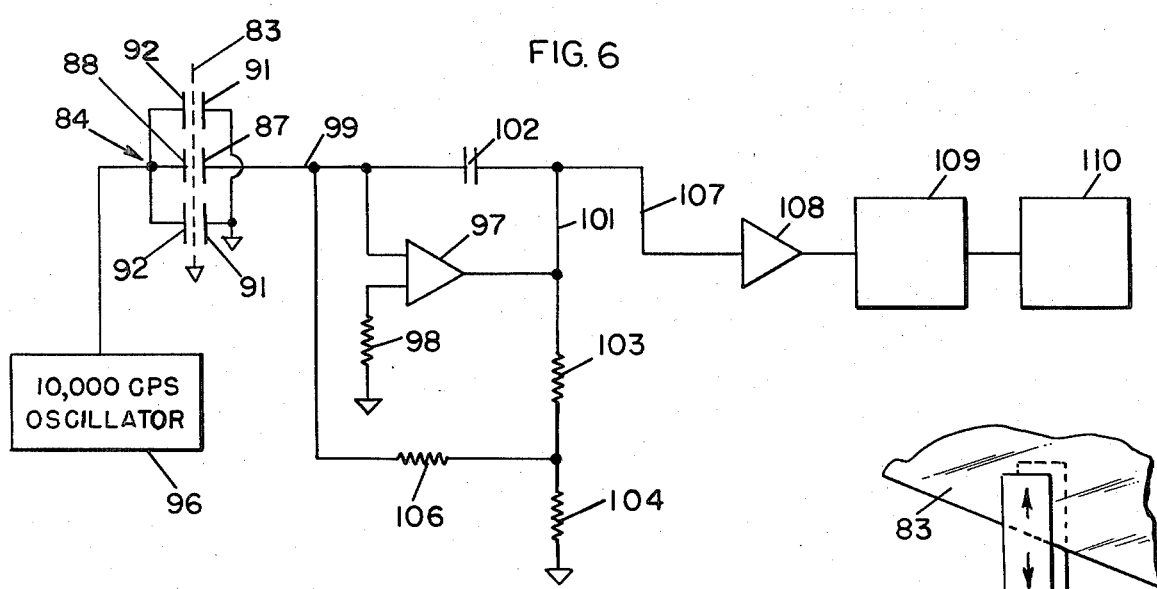
FIG. 8 is a block diagram of the transducer and electronic readout circuit incorporated in the viscosimeter of FIG. 1.
Figure 9:
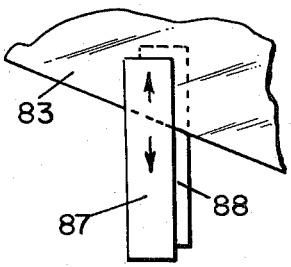
FIG. 9 is a schematic illustration of a portion of the viscosimeter of the invention.
Figure 7:
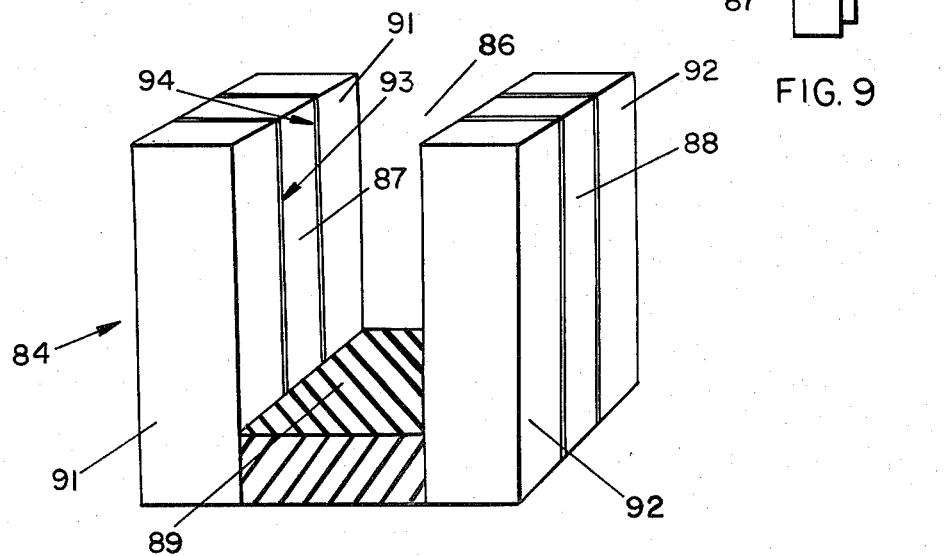
FIG. 7 is an enlarged perspective view of the capacitor utilized in the transducer of FIG. 6.

Referring now to FIG. 8, there is shown one embodiment of a circuit for providing the electronic readout means of the invention incorporating the transducer 84. In the circuit of FIG. 8, the transducer 84 is driven by an oscillator 96, the output of which is connected to one of the plates 88 of the capacitor 84. Any suitable excitation frequency may be chosen for the capacitor 84 such as a frequency within the range of 10 kHz to 100 kHz. In the illustrated embodiment, the transducer 84 may have a capacitance of approximately 1 pF usable capacitance at full scale.

The circuit of FIG. 8 includes a preamplifier 97 having one input connected to ground through a resistor 98 and the other input to the opposite side of the capacitor 84 from the oscillator 96 by means of conductor 99. The ouput of preamplifier 97 is connected to conductor 101 connected through capacitor 102 to conductor 99 and through a voltage divider comprising resistors 103, 104 to ground. The junction point of the voltage divider 103, 104 is connected through resistor 106 to the capacitor 84 through conductor 99. The junction point of conductor 101 and the capacitor 102 is connected by conductor 107 to the input of a scaling amplifier and AC/DC converter 108, one output of which is connected to the input of an adjustable second-order filter 109. The output of filter 109 is connected to a suitable meter 110 on which the measured viscosity of the liquid sample is indicated.

The circuit of FIG. 8 has many advantages over the prior art in that it is frequency independent and is functionally independent of the length of the coaxial cables used to connect the preamplifier to the transducer. Furthermore, the electronic readout means embodied in the circuit of FIG. 8 provides for the electronic setting of zero and the use of electronic damping to remove troublesome oscillations from the signal. Because the interfering oscillations are analytically an exponentially decaying sine wave, they may be effectively removed by filters without introducing error. The second-order filter 109 in the circuit of FIG. 8 is preferably a Butterworth filter with a variable bandpass.

In the operation of the viscosimeter V of the invention, with the parts arranged in the manner shown in FIG. 1 and with the liquid to be tested in the cup 13, the cup containing the liquid sample is rotated at a constant speed and is maintained at a constant temperature by the rotating hot plate 12. As the cup 13 with the sample contained therein rotates, the spindle and torsion wire assembly also rotate due to the drag of the liquid sample on the plunger 27. The spindle 26 rotates until the restoring force of the torsion wire 23 just balances the drag of the liquid and when the spindle 26 stops, the ramp 83 occupies a corresponding portion of the gap 86 in the transducer or capacitor 84. The output signal from the transducer 84 is subsequently preamplified and conditioned in the circuit of FIG. 8, thereby providing an accurate measurement on the meter 110 of the liquid in the cup 13.

The foregoing relates to a preferred exemplary embodiment of the invention, it being understood that other embodiments and variants thereof are possible within the spirit and scope of the invention, the latter being defined by the appended claims.

What is claimed and desired to be secured by Letters Patent of the United States is:

1. A viscosimeter for measuring the viscosity of liquids comprising, in combination, a base, a container for the liquid to be tested rotatably mounted on said base, means for heating the liquid in said container, an upstanding support member having an upper end mounted on said base, a torsion wire arranged to be detachably mounted at its upper end on said support member in a vertically extending position, a plunger detachably mounted on the lower end of said torsion wire for immersion in the liquid in said container, a vertically extending spindle operatively attached and mounted on said support member to form a torsion wire and spindle assembly whereby rotation of said container rotates said spindle and torsion wire assembly into an angular position corresponding to the drag of the liquid on said plunger immersed therein, transducer means for electrically sensing said angular position of said spindle and torsion wire, electronic readout means connected to said transducer means for indicating the viscosity of the liquid in said container, said transducer means comprises an arcuate plate having an inclined lower edge portion supported on said torsion wire and spindle assembly and a capacitor having a pair of spaced plates defining a gap and wherein said arcuate plate lower edge portion is disposed within said gap to a variable extent as determined by the angular position of said torsion wire and spindle assembly.

2. A viscosimeter in accordance with claim 1, wherein said transducer means is of the capacitive type.

3. A viscosimeter in accordance with claim 1, including a coupling sleeve of heat insulation material having an upper and a lower end, means for detachably coupling said plunger to said coupling sleeve lower end and means for detachably coupling the upper end of said coupling sleeve to the lower end of said torsion wire and spindle assembly.

4. A viscosimeter in accordance with claim 3, including releasable clamping means mounted on said support member for clamping engagement with said torsion wire and spindle assembly.

5. A viscosimeter in accordance with claim 4, wherein said support member includes an upper section and a lower section, adjustable means for mounting said support member upper section on said lower section for positioning said upper section in an adjusted vertical position to thereby position said plunger in said liquid at a selected level.

* * * * *